(12) United States Patent
Muehlsteff et al.

(10) Patent No.: US 11,298,033 B2
(45) Date of Patent: Apr. 12, 2022

(54) NON-INVASIVE BLOOD PRESSURE MONITORS AND METHODS OF OPERATING THE SAME

(71) Applicant: KONINKLIJKE PHILIPS N.V., Eindhoven (NL)

(72) Inventors: Jens Muehlsteff, Aachen (DE); Teun Van Den Heuvel, Eindhoven (NL); Erik Bresch, Eindhoven (NL); Lars Schmitt, Aachen (DE); Dieter Woehrle, Waiblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 421 days.

(21) Appl. No.: 16/405,318

(22) Filed: May 7, 2019

(65) Prior Publication Data

US 2019/0328240 A1      Oct. 31, 2019

Related U.S. Application Data

(63) Continuation of application No. 14/857,892, filed on Sep. 18, 2015, now abandoned.

(30) Foreign Application Priority Data

Oct. 10, 2014   (EP) .................................. 14188414

(51) Int. Cl.
*A61B 5/022* (2006.01)
*A61B 5/02* (2006.01)
(Continued)

(52) U.S. Cl.
CPC .............. *A61B 5/022* (2013.01); *A61B 5/024* (2013.01); *A61B 5/02028* (2013.01);
(Continued)

(58) Field of Classification Search
CPC ............................................ A61B 5/022–0235
See application file for complete search history.

(56) References Cited

U.S. PATENT DOCUMENTS

| | | | |
|---|---|---|---|
| 6,423,010 B1 | 7/2002 | Friedman | A61B 5/021 600/493 |
| 8,734,355 B2 | 5/2014 | Whitaker | A61B 5/02233 600/490 |

(Continued)

FOREIGN PATENT DOCUMENTS

| | | |
|---|---|---|
| CN | 101810470 A | 8/2010 |
| CN | 103211586 A | 7/2013 |

(Continued)

OTHER PUBLICATIONS

Dogra, R. "'Orthoryhthmia' or postural cardiac dysrhythmia: clinical significance." J Assoc Physicians India. May 1996;44(5):316-9.

(Continued)

*Primary Examiner* — Meredith Weare

(57) ABSTRACT

According to an aspect, there is provided a method of operating a non-invasive blood pressure, NIBP, monitor to measure the blood pressure of a subject, the NIBP monitor comprising a cuff, a pressure sensor for measuring the pressure in the cuff and for outputting a pressure signal representing the pressure in the cuff and a physiological parameter sensor, the method comprising obtaining a first measurement of a physiological parameter for the subject during inflation of the cuff, the first measurement being obtained from the pressure signal; obtaining a second measurement of the physiological parameter for the subject during inflation of the cuff, the second measurement being obtained from the physiological parameter sensor; comparing the first measurement and the second measurement; and estimating the reliability of a blood pressure measurement (Continued)

Estimate the risk of arrhythmia occurring in the subject during a scheduled BP measurement — 111

Adapt the scheduled BP measurement according to the estimated risk — 113 obtained by the NIBP monitor during inflation of the cuff based on the result of the step of comparing.

5 Claims, 6 Drawing Sheets

(51) Int. Cl.
*A61B 5/00* (2006.01)
*A61B 5/021* (2006.01)
*A61B 5/024* (2006.01)

(52) U.S. Cl.
CPC ...... *A61B 5/02141* (2013.01); *A61B 5/02225* (2013.01); *A61B 5/7221* (2013.01); *A61B 5/7275* (2013.01); *A61B 5/74* (2013.01); *A61B 2560/0266* (2013.01)

(56) References Cited

U.S. PATENT DOCUMENTS

| | | | |
|---|---|---|---|
| 2002/0002338 A1 | 1/2002 | Palma | A61B 5/022 600/485 |
| 2002/0016550 A1 | 2/2002 | Sweeney | A61N 1/3622 600/515 |
| 2003/0060721 A1 | 3/2003 | Nakazawa | A61B 5/0002 600/490 |
| 2005/0033188 A1 | 2/2005 | Whitaker | A61B 5/02233 600/490 |
| 2005/0283083 A1 | 12/2005 | Lee et al. | |
| 2008/0045846 A1 | 2/2008 | Friedman et al. | |
| 2008/0208064 A1 | 8/2008 | Lee | A61B 5/024 600/485 |
| 2008/0281211 A1 | 11/2008 | Whitaker | A61B 5/02233 600/490 |
| 2009/0043179 A1* | 2/2009 | Melker | A61B 5/02416 600/323 |
| 2010/0331713 A1 | 12/2010 | Ostrow | A61B 5/0031 600/518 |
| 2011/0152700 A1 | 6/2011 | Sawanoi et al. | |
| 2011/0160597 A1 | 6/2011 | Lane | A61B 5/02225 600/493 |
| 2012/0046561 A1 | 2/2012 | Usuda | A61B 5/02116 600/494 |
| 2012/0078126 A1 | 3/2012 | Jarrell | A61B 5/02007 600/494 |
| 2012/0149994 A1 | 6/2012 | Luczyk | A61B 5/02225 600/301 |
| 2012/0157791 A1* | 6/2012 | Hersh | A61B 5/024 600/301 |
| 2012/0323128 A1 | 12/2012 | Ma | |
| 2012/0330112 A1 | 12/2012 | Lamego et al. | |
| 2016/0100805 A1 | 4/2016 | Muehlsteff et al. | |

FOREIGN PATENT DOCUMENTS

| | | |
|---|---|---|
| EP | 1779773 A2 | 5/2007 |
| EP | 2198773 A1 | 6/2010 |
| JP | 2006212178 | 8/2006 |
| WO | 2013170095 A1 | 11/2013 |
| WO | 2014018024 A1 | 1/2014 |

OTHER PUBLICATIONS

Havlik, et al., "Detection of artifacts in oscillometric pulsations signals", EIII-EMBS International Conference on Biomedical and Health Informatics (BHI), IEEE, Jun. 1, 2014.

Geddes, L. A., et al.; Characterization of the oscillometric method for measuring indirect blood pressure; 1982; Annals of Biomedical Engineering; 10(6)271-280.

* cited by examiner

NON-INVASIVE BLOOD PRESSURE MONITORS AND METHODS OF OPERATING THE SAME

CROSS REFERENCE TO RELATED APPLICATIONS

This application claims the benefit of U.S. patent application Ser. No. 14/857,892 filed Sep. 18, 2015, which claims the benefit of EP provisional application serial no. 14188414.8 filed Oct. 10, 2014, which is incorporated herein by reference.

TECHNICAL FIELD OF THE INVENTION

The invention relates to non-invasive blood pressure (NIBP) monitors and methods of operating the same, and in particular relates to improving the accuracy of the blood pressure measurements obtained by such monitors and methods.

BACKGROUND TO THE INVENTION

Arterial blood pressure (BP) is one of the most important vital signs and is widely used in clinical practice. Non-invasive arterial blood pressure (NIBP) is usually measured by slowly varying the pressure in a cuff that is wrapped around the upper arm of a subject. The BP is determined either by measuring sound distal from the cuff (the auscultatory method, based on Korotkoff sounds) or by measuring pressure pulsations in the cuff caused by volume pulsations of the arm and brachial artery and extracting features from the envelope of these pressure pulses (the oscillometric method). The oscillometric method is easily automated and is widely used.

The principle behind a typical oscillometric method is illustrated by FIG. 1, which shows a graph of cuff pressure 10, and a processed high pass filtered trace 12 of this cuff pressure, versus time. The left-hand y-axis shows pulse amplitude, the right-hand y-axis shows cuff pressure, and the x-axis shows time. To perform a NIBP measurement using the oscillometric method, first the cuff pressure 10 is ramped up until it is sufficiently larger than systolic blood pressure. After ramp up, the cuff is deflated (in FIG. 1 the deflation is done gradually, but step wise deflation is also possible). During the deflation, small oscillations in cuff pressure occur, caused by volume changes in the bladder of the cuff, which are in turn caused by volume changes in the brachial artery. The measured cuff pressure 10 is high pass filtered, and the resulting trace 12 shows the cuff pressure oscillations due to volume changes in the brachial artery. An envelope 14 of the oscillation amplitudes is determined. The maximum $A_{max}$ of this pulse envelope 14 is taken as a reference point for determining the systolic 16 and diastolic pressure 15. The systolic pressure 16 is determined as the cuff pressure where the pressure oscillation is approximately 0.8 times the maximum amplitude $A_{max}$ at a pressure higher than the pressure at the reference point. The diastolic pressure 15 is determined as the cuff pressure where the pressure oscillation is approximately 0.55 times the maximum amplitude $A_{max}$ at a pressure lower than the pressure at the reference point. These ratios are based on empirical values (see, e.g., L A Geddes et. al., Annals of Biomedical Engineering 10 pp 271-280, 1982). The exact algorithms that are employed by manufacturers of blood pressure devices to determine systolic and diastolic pressures are usually trade secrets.

The typical monitor 20 used for acquiring oscillometric NIBP measurements is illustrated in FIG. 2. A pump 22, a pressure sensor 24, and a valve 26 are connected to a cuff 28 by tubing 30. A control unit 32 is connected to the pump 22 and the valve 26 to control the operation of those components, and is also connected to the pressure sensor 24 in order to receive the signal representing the pressure of the gas in the cuff 28 (the 'pressure signal'). The control unit 32 runs the algorithm that controls the pump 22 and valve 26 and processes the pressure signal from the pressure sensor 24 to determine the BP measurement. During execution of the oscillometric method the pump 22 blows air into the cuff 28, thereby inflating it. The pressure sensor 24 measures the gas pressure in the system (and therefore the pressure of the gas in the cuff 28) and outputs a signal representing the pressure in the cuff 28 (referred to as the 'pressure signal'). When a pressure larger than systolic pressure is reached, the pump 22 is disabled or switched off, the valve 26 is opened and slow (or step wise) deflation occurs, during which the cuff pressure is continuously measured and the measurements (pressure signal) stored. The pump 22 and valve 26 are controlled by a control unit 32, which also receives the cuff pressure measurements and calculates the pulse envelope and the systolic and diastolic pressure using these measurements. In practice the monitor 20 may comprise multiple sensors and valves for safety reasons.

The operation of the typical monitor 20 is often uncomfortable for the subject (and in some cases is painful), since the arm is compressed with an external pressure. In a clinical or hospital (or even home) setting where blood pressure measurements need to be obtained through the day and night, the taking of a blood pressure measurement by the monitor 20 will often disturb the sleep of the subject. NIBP monitors originally developed for high acuity subjects (e.g. those in an intensive care unit (ICU)) were optimized for accuracy and precision, but not the comfort of the subject.

In a home setting, it has been found that NIBP measurements have a relatively low acceptance by subjects (e.g. the subjects do not comply with the required measurement schedule or do not perform the measurements properly), which in some cases is due to the pain caused by the inflation of the cuff (which can relate to the duration that the cuff is inflated for and/or the peak pressure in the cuff), irritation of skin under the cuff (particularly on NIBP monitors that are continuously worn by a subject), haematomas, and disturbance of the sleep of the subject.

The comfort of the NIBP measurement can be improved in any or all of three areas: the total measurement time (where a reduction is desired), the maximum cuff pressure reached (where a lower maximum pressure is desired) and the integral of cuff pressure over time (where a smaller integral is desired). Of course, this increase in comfort should not come at the expense of the accuracy of the NIBP measurement beyond acceptable limits.

In addition to the types of monitor described above in which the BP is measured using envelope detection during deflation of the cuff (which can typically take around 45 seconds), monitors have been developed that can measure the BP while the cuff is being inflated. This can reduce the total measurement time (in some cases to around 20 seconds), since the deflation stage can be very quick once the BP measurement has been obtained, and therefore can result in a measurement that is more comfortable for the subject. However, currently available algorithms for measuring BP during the inflation of the cuff are not as accurate as conventional deflation-based algorithms, as inflation-based measurements are susceptible to measurement artefacts arising from movements by the subject or arrhythmias.

Therefore there is a need for an NIBP monitor and method of operating the same that measures the blood pressure during inflation of the cuff and that provides improved accuracy of the blood pressure measurement compared to conventional monitors.

SUMMARY OF THE INVENTION

According to a first aspect, there is provided a method of operating a non-invasive blood pressure, NIBP, monitor to measure the blood pressure of a subject, the NIBP monitor comprising a cuff, a pressure sensor for measuring the pressure in the cuff and for outputting a pressure signal representing the pressure in the cuff and a physiological parameter sensor, the method comprising obtaining a first measurement of a physiological parameter for the subject during inflation of the cuff, the first measurement being obtained from the pressure signal; obtaining a second measurement of the physiological parameter for the subject during inflation of the cuff, the second measurement being obtained from the physiological parameter sensor; comparing the first measurement and the second measurement; and estimating the reliability of a blood pressure measurement obtained by the NIBP monitor during inflation of the cuff based on the result of the step of comparing.

In some embodiments, the step of obtaining a second measurement of the physiological parameter is performed at the same time or within a certain time window as the step of obtaining the first measurement.

In some embodiments, the method further comprises the step of correcting the timing of one of the first and second measurements to account for time delays in obtaining said measurement.

In some embodiments, the step of estimating the reliability is performed before a blood pressure measurement is obtained by the NIBP monitor.

In some embodiments, the method further comprises the step of determining whether to obtain a blood pressure measurement during inflation of the cuff or during deflation of the cuff based on the estimated reliability. In some embodiments, the step of determining comprises determining that a blood pressure measurement should be obtained during inflation of the cuff if a blood pressure measurement obtained by the NIBP monitor during inflation of the cuff is estimated to be reliable. In some embodiments, the step of determining comprises determining that a blood pressure measurement should be obtained during deflation of the cuff if a blood pressure measurement obtained by the NIBP monitor during inflation of the cuff is estimated to be unreliable.

In some embodiments, the method further comprises the step of discarding a blood pressure measurement obtained by the NIBP monitor during inflation of the cuff, or marking said measurement as unreliable, if the blood pressure measurement is estimated to be unreliable.

In some embodiments, the step of comparing the first measurement and the second measurement comprises evaluating the numerical difference between the first measurement and the second measurement or evaluating how close the first measurement matches the second measurement.

In some embodiments, where a blood pressure measurement that is to be obtained by the NIBP monitor during inflation of the cuff is scheduled for a particular time, the method further comprises the steps of estimating the risk of arrhythmia occurring in the subject during the scheduled blood pressure measurement; and adapting the scheduled blood pressure measurement according to the estimated risk.

In some embodiments, the step of adapting comprises determining whether to reschedule the scheduled blood pressure measurement to a different time based on the estimated risk. In some embodiments, the step of adapting comprises rescheduling the scheduled blood pressure measurement to a different time if the estimated risk is too high.

In some embodiments, the step of adapting comprises determining whether to perform the blood measurement during deflation of the cuff instead of during inflation of the cuff based on the estimated risk. In some embodiments, the step of adapting comprises performing the scheduled blood pressure measurement during deflation of the cuff instead of during inflation of the cuff if the estimated risk is too high.

In some embodiments, the step of estimating the risk of arrhythmia comprises analyzing the occurrence of arrhythmias in the subject to provide an estimate of when future arrhythmias are likely to occur; and wherein the estimate of the risk of an arrhythmia occurring in the subject during the scheduled blood pressure measurement is based on the estimate of when future arrhythmias are likely to occur.

In some embodiments, the step of estimating the risk of arrhythmia comprises determining the posture of the subject.

In some embodiments, the step of adapting the scheduled blood pressure measurement according to the estimated risk comprises delaying the scheduled blood measurement if the subject is determined to be in an incorrect posture or a non-preferred posture for the blood pressure measurement.

In some embodiments, the step of adapting the scheduled blood pressure measurement according to the estimated risk comprises performing the scheduled blood pressure measurement during deflation of the cuff if the subject is determined to be in an incorrect posture or a non-preferred posture for performing a blood pressure measurement during inflation of the cuff.

In some embodiments, the step of estimating the risk of arrhythmia comprises determining the recent activity level of the subject.

In some embodiments, the step of adapting the scheduled blood pressure measurement according to the estimated risk comprises delaying the scheduled blood measurement if the subject is determined to have recently engaged in an activity.

In some embodiments, the step of adapting the scheduled blood pressure measurement according to the estimated risk comprises performing the scheduled blood pressure measurement during deflation of the cuff if the subject is determined to have recently engaged in an activity.

In some embodiments, the physiological parameter sensor is a different sensor to the sensor that measures the pressure in the cuff.

In some embodiments, the physiological parameter is a parameter relating to the heart of the subject.

In some embodiments the physiological parameter is the pulse rate, heart rate or other parameter representing the beating of the heart of the subject.

In some embodiments the physiological parameter sensor is a photoplethysmography, PPG sensor, an accelerometer or an electrocardiograph, ECG, sensor.

In some embodiments the physiological parameter sensor is integrated with the cuff. In other embodiments the physiological parameter sensor is physically separate from the cuff.

According to a second aspect, there is provided a computer program product comprising a computer readable medium having computer readable code embodied therein, the computer readable code being configured such that, on execution by a suitable computer, processor or control unit, the computer, processor or control unit is caused to perform any of the methods described above.

According to a third aspect, there is provided a non-invasive blood pressure, NIBP, monitor for measuring the blood pressure of a subject, the NIBP monitor comprising a cuff; a pressure sensor for measuring the pressure in the cuff and for outputting a pressure signal representing the pressure in the cuff; a physiological parameter sensor for measuring a physiological parameter; and a control unit that is configured to obtain a first measurement of a physiological parameter for the subject during inflation of the cuff, the first measurement being obtained from the pressure signal; obtain a second measurement of the physiological parameter for the subject during inflation of the cuff, the second measurement being obtained from the physiological parameter sensor; compare the first measurement and the second measurement; and estimate the quality of a blood pressure measurement obtained by the NIBP monitor during inflation of the cuff based on the result of the comparison.

In some embodiments, the control unit is configured to obtain a second measurement of the physiological parameter at the same time or within a certain time window as the first measurement.

In some embodiments, the control unit is further configured to correct the timing of one of the first and second measurements to account for time delays in obtaining said measurement.

In some embodiments, the control unit is configured to estimate the reliability before a blood pressure measurement is obtained by the NIBP monitor.

In some embodiments, the control unit is further configured to determine whether to obtain a blood pressure measurement during inflation of the cuff or during deflation of the cuff based on the estimated reliability.

In some embodiments, the control unit is configured to determine that a blood pressure measurement should be obtained during inflation of the cuff if a blood pressure measurement obtained by the NIBP monitor during inflation of the cuff is estimated to be reliable. In some embodiments, the control unit is configured to determine that a blood pressure measurement should be obtained during deflation of the cuff if a blood pressure measurement obtained by the NIBP monitor during inflation of the cuff is estimated to be unreliable.

In some embodiments, the control unit is configured to discard a blood pressure measurement obtained by the NIBP monitor during inflation of the cuff, or mark said measurement as unreliable, if the blood pressure measurement is estimated to be unreliable.

In some embodiments, the control unit is configured to compare the first measurement and the second measurement by evaluating the numerical difference between the first measurement and the second measurement or evaluating how close the first measurement matches the second measurement.

In some embodiments, the control unit is configured to obtain a blood pressure measurement during inflation of the cuff at a scheduled time, and the control unit is further configured to estimate the risk of arrhythmia occurring in the subject during the scheduled blood pressure measurement; and adapt the scheduled blood pressure measurement according to the estimated risk.

In some embodiments, the control unit is configured to adapt the scheduled blood pressure measurement by determining whether to reschedule the scheduled blood pressure measurement to a different time based on the estimated risk.

In some embodiments, the control unit is configured to adapt the scheduled blood pressure measurement by rescheduling the scheduled blood pressure measurement to a different time if the estimated risk is too high.

In some embodiments, the control unit is configured to adapt the scheduled blood pressure measurement by determining whether to perform the blood measurement during deflation of the cuff instead of during inflation of the cuff based on the estimated risk.

In some embodiments, the control unit is configured to adapt the scheduled blood pressure measurement by performing the scheduled blood pressure measurement during deflation of the cuff instead of during inflation of the cuff if the estimated risk is too high.

In some embodiments, the control unit is configured to estimate the risk of arrhythmia by analyzing the occurrence of arrhythmias in the subject to provide an estimate of when future arrhythmias are likely to occur; and wherein the estimate of the risk of an arrhythmia occurring in the subject during the scheduled blood pressure measurement is based on the estimate of when future arrhythmias are likely to occur.

In some embodiments, the control unit is configured to estimate the risk of arrhythmia by determining the posture of the subject.

In some embodiments, the control unit is configured to adapt the scheduled blood pressure measurement according to the estimated risk by delaying the scheduled blood measurement if the subject is determined to be in an incorrect or non-preferred posture for the blood pressure measurement.

In some embodiments, the control unit is configured to adapt the scheduled blood pressure measurement according to the estimated risk by performing the scheduled blood pressure measurement during deflation of the cuff if the subject is determined to be in an incorrect or non-preferred posture for performing a blood pressure measurement during inflation of the cuff.

In some embodiments, the control unit is configured to estimate the risk of arrhythmia by determining the recent activity level of the subject.

In some embodiments, the control unit is configured to adapt the scheduled blood pressure measurement according to the estimated risk by delaying the scheduled blood measurement if the subject is determined to have recently engaged in an activity.

In some embodiments, the control unit is configured to adapt the scheduled blood pressure measurement according to the estimated risk by performing the scheduled blood pressure measurement during deflation of the cuff if the subject is determined to have recently engaged in an activity.

According to a fourth aspect, there is provided a method of measuring the blood pressure of a subject using a non-invasive blood pressure, NIBP, monitor, the method comprising estimating the risk of arrhythmia occurring in the subject during a scheduled blood pressure measurement; and adapting the scheduled measurement of the blood pressure according to the estimated risk.

In some embodiments, the step of adapting comprises determining whether to reschedule the scheduled blood pressure measurement to a different time based on the estimated risk. In some embodiments, the step of adapting comprises rescheduling the scheduled blood pressure measurement to a different time if the estimated risk is too high.

In some embodiments, the step of adapting comprises determining whether to perform the blood measurement during deflation of the cuff instead of during inflation of the cuff based on the estimated risk. In some embodiments, the step of adapting comprises performing the scheduled blood pressure measurement during deflation of the cuff instead of during inflation of the cuff if the estimated risk is too high.

In some embodiments, the step of estimating the risk of arrhythmia comprises analyzing the occurrence of arrhythmias in the subject to provide an estimate of when future arrhythmias are likely to occur; and wherein the estimate of the risk of an arrhythmia occurring in the subject during the scheduled blood pressure measurement is based on the estimate of when future arrhythmias are likely to occur.

In some embodiments, the step of estimating the risk of arrhythmia comprises determining the posture of the subject.

In some embodiments, the step of adapting the scheduled blood pressure measurement according to the estimated risk comprises delaying the scheduled blood measurement if the subject is determined to be in an incorrect posture or a non-preferred posture for the blood pressure measurement.

In some embodiments, the step of adapting the scheduled blood pressure measurement according to the estimated risk comprises performing the scheduled blood pressure measurement during deflation of the cuff if the subject is determined to be in an incorrect posture or a non-preferred posture for performing a blood pressure measurement during inflation of the cuff.

In some embodiments, the step of estimating the risk of arrhythmia comprises determining the recent activity level of the subject.

In some embodiments, the step of adapting the scheduled blood pressure measurement according to the estimated risk comprises delaying the scheduled blood measurement if the subject is determined to have recently engaged in an activity.

In some embodiments, the step of adapting the scheduled blood pressure measurement according to the estimated risk comprises performing the scheduled blood pressure measurement during deflation of the cuff if the subject is determined to have recently engaged in an activity.

According to a fifth aspect, there is provided a computer program product comprising a computer readable medium having computer readable code embodied therein, the computer readable code being configured such that, on execution by a suitable computer, processor or control unit, the computer, processor or control unit is caused to perform any of the methods described above.

According to a sixth aspect, there is provided a non-invasive blood pressure, NIBP, monitor for measuring the blood pressure of a subject, the NIBP monitor comprising a control unit that is configured to obtain a blood pressure measurement during inflation of a cuff at a scheduled time; estimate the risk of arrhythmia occurring in the subject during the scheduled blood pressure measurement; and adapt the scheduled blood pressure measurement according to the estimated risk.

In some embodiments, the control unit is configured to adapt the scheduled blood pressure measurement by determining whether to reschedule the scheduled blood pressure measurement to a different time based on the estimated risk.

In some embodiments, the control unit is configured to adapt the scheduled blood pressure measurement by rescheduling the scheduled blood pressure measurement to a different time if the estimated risk is too high.

In some embodiments, the control unit is configured to adapt the scheduled blood pressure measurement by determining whether to perform the blood measurement during deflation of the cuff instead of during inflation of the cuff based on the estimated risk.

In some embodiments, the control unit is configured to adapt the scheduled blood pressure measurement by performing the scheduled blood pressure measurement during deflation of the cuff instead of during inflation of the cuff if the estimated risk is too high.

In some embodiments, the control unit is configured to estimate the risk of arrhythmia by analyzing the occurrence of arrhythmias in the subject to provide an estimate of when future arrhythmias are likely to occur; and wherein the estimate of the risk of an arrhythmia occurring in the subject during the scheduled blood pressure measurement is based on the estimate of when future arrhythmias are likely to occur.

In some embodiments, the control unit is configured to estimate the risk of arrhythmia by determining the posture of the subject.

In some embodiments, the control unit is configured to adapt the scheduled blood pressure measurement according to the estimated risk by delaying the scheduled blood measurement if the subject is determined to be in an incorrect or non-preferred posture for the blood pressure measurement.

In some embodiments, the control unit is configured to adapt the scheduled blood pressure measurement according to the estimated risk by performing the scheduled blood pressure measurement during deflation of the cuff if the subject is determined to be in an incorrect or non-preferred posture for performing a blood pressure measurement during inflation of the cuff.

In some embodiments, the control unit is configured to estimate the risk of arrhythmia by determining the recent activity level of the subject.

In some embodiments, the control unit is configured to adapt the scheduled blood pressure measurement according to the estimated risk by delaying the scheduled blood measurement if the subject is determined to have recently engaged in an activity.

In some embodiments, the control unit is configured to adapt the scheduled blood pressure measurement according to the estimated risk by performing the scheduled blood pressure measurement during deflation of the cuff if the subject is determined to have recently engaged in an activity.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As described above, measuring the blood pressure (BP) of a subject during inflation of a cuff, rather than during deflation of the cuff from a peak pressure that is sufficient to prevent blood flow in the limb, allows the BP measurement to be completed more quickly, which helps to improve the comfort of the BP measurement for the subject.

However, currently available algorithms for measuring BP during the inflation of the cuff are not as accurate as conventional deflation-based algorithms, as inflation-based measurements are susceptible to measurement artefacts arising from movements by the subject or arrhythmias. Therefore aspects of the invention provide ways to ascertain the accuracy or quality of BP measurements obtained during inflation of the cuff. In particular, in certain aspects, during the inflation of the cuff, a physiological parameter for the subject is determined from the pressure signal representing the pressure in the cuff, and this physiological parameter is compared to a measurement of the same physiological parameter obtained using a separate/dedicated sensor. The closer the physiological parameter obtained from the pressure signal is to the measurement of the physiological parameter from the separate/dedicated sensor, the more likely it is that the BP measurement obtained during inflation of the cuff will be accurate. In certain embodiments, if a comparison of the measurements of the physiological parameter suggests that the BP measurement is not sufficiently accurate, the BP measurement can be stopped (if the BP measurement has not yet been completed), the BP measurement can be discarded (i.e. not reported to the subject/care provider/user, base unit or remote computer) and/or an error output by the monitor, or the monitor can switch to taking a BP measurement using a conventional deflation-based algorithm, since these measurements are less susceptible to measurement artefacts that can affect BP measurements obtained during inflation of the cuff.

Figure 1:
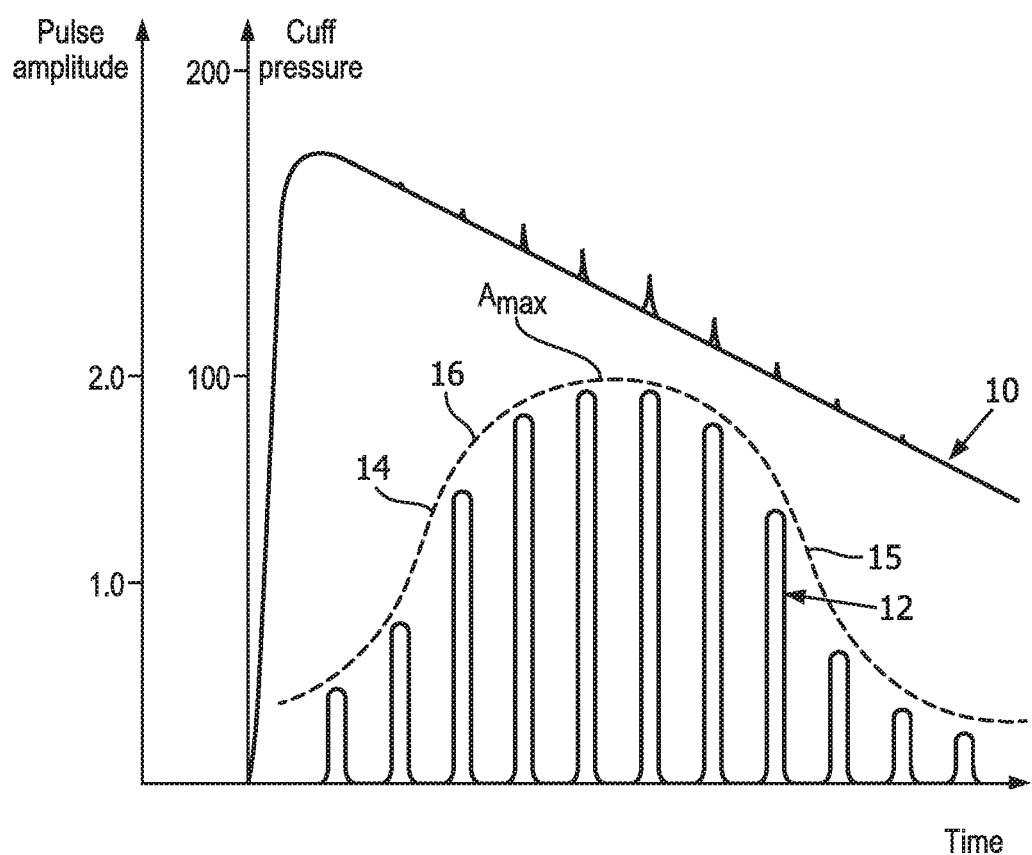
FIG. 1 is a graph of cuff pressure versus time measured using a conventional oscillometric NIBP monitor.
Figure 2:
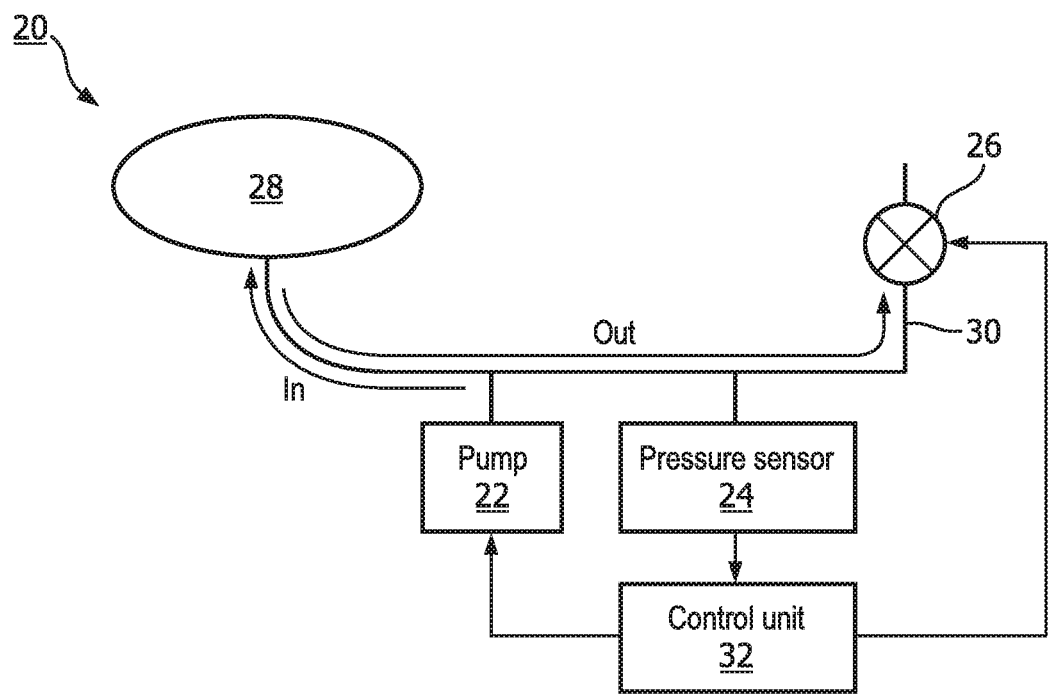
FIG. 2 shows a block diagram of a conventional oscillatory NIBP monitor.
Figure 3:
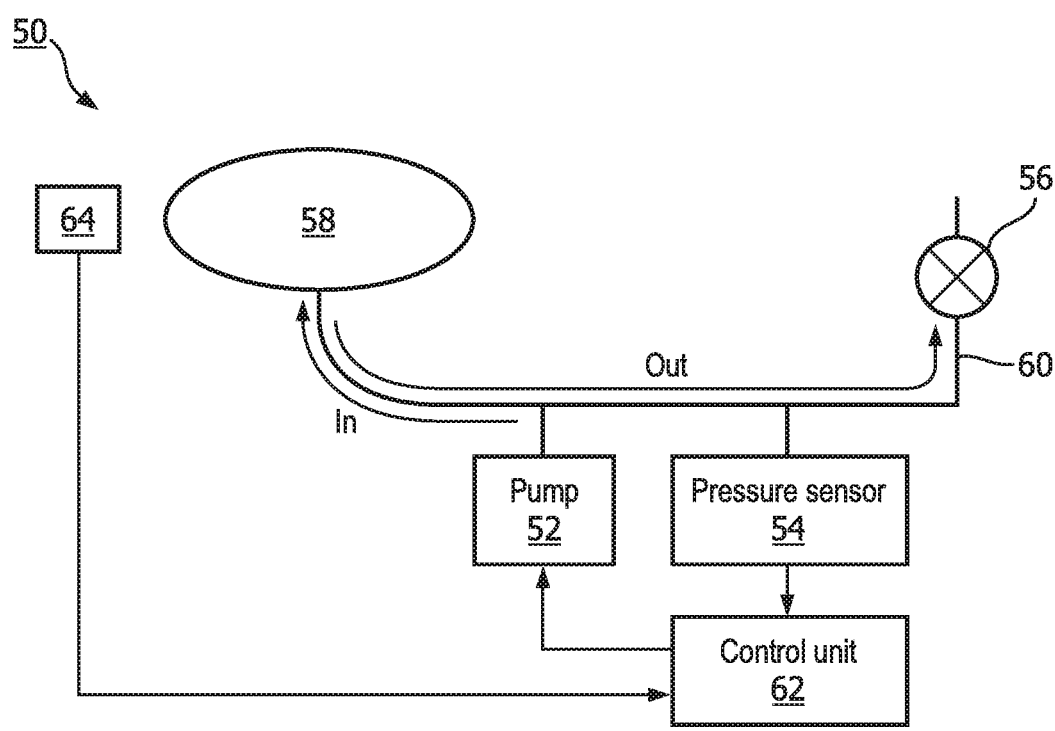
FIG. 3 is a block diagram of an NIBP monitor according to an embodiment of the invention.

A non-invasive blood pressure (NIBP) monitor according to an embodiment of the invention is shown in FIG. 3. The monitor 50 comprises a pump 52, a pressure sensor 54, and a valve 56 that are connected to a cuff 58 by tubing 60. A control unit 62 is connected to the pump 52 and the valve 56 to control the operation of those components, and is also connected to the pressure sensor 54 in order to receive the signal representing the pressure of the gas in the cuff 58 (the 'pressure signal'). The control unit 62 runs the algorithm that controls the pump 52 and valve 56 and processes the pressure signal from the pressure sensor 54 to determine the BP measurement.

As in the conventional monitor, the pump 52 is for blowing air or other gas into the cuff 58 in order to inflate the cuff 58 and prevent blood flow in the limb around which the cuff 58 is placed. The valve 56 is used to allow air or gas out of the system and thus deflate the cuff 58.

In accordance with an embodiment of the invention, the monitor 50 further comprises a physiological parameter sensor 64 that is for measuring a physiological parameter of the subject while the cuff 58 is being inflated. The physiological parameter sensor 64 can be any type of sensor that measures a physiological parameter of the subject that can also be derived from the pressure signal from the cuff 58.

In preferred embodiments, the physiological parameter is a parameter relating to the heart of the subject, and even more preferably the physiological parameter is the pulse rate or heart rate of the subject. Accordingly, in preferred embodiments, the sensor 64 is a sensor for measuring a heart parameter of the subject, and even more preferably the sensor 64 is a sensor for measuring the pulse rate, heart rate or beating of the heart of the subject. For example, the sensor 64 can be a pulse or heart beat sensor such as a photoplethysmography (PPG) sensor, an accelerometer, an ECG sensor, although those skilled in the art will be aware of other types of heart rate sensor that can be used (such as a camera, radar, impedance cardiogram, heart sound sensor, etc.). In the case of a PPG sensor, accelerometer and/or ECG sensor, the sensor 64 can comprise the appropriate sensing apparatus, e.g. light source and detector for a PPG sensor, accelerometer, and two or more electrodes for an ECG sensor, and the processing of the signals from those sensors to determine the pulse rate, heart rate or a signal representing the heart beats (so that arrhythmias can be identified) can be performed by the control unit 62. In the case of an accelerometer, the acceleration signal can be processed to extract the movements caused by the beating of the heart/pulses of blood in the circulatory system.

In use, the physiological parameter sensor 64 is attached to or otherwise in contact with the appropriate part of the body of the subject in order to measure the physiological parameter. It will be appreciated that in some embodiments, the sensor 64 can be integrated with the cuff 58 so the subject only has to place the cuff around their arm in order to start using the monitor 50, whereas in other embodiments the sensor 64 can be physically separate from the cuff 58 and placed separately on the body of the subject. In some embodiments, there can be a wired connection between the sensor 64 and the control unit 62, whereas in other embodiments, the sensor 64 can communicate with the control unit 62 wirelessly.

It will be appreciated that FIG. 3 only shows the components required to illustrate this aspect of the invention, and in a practical implementation the NIBP monitor 50 will comprise additional components to those shown. For example, the monitor 50 may comprise multiple pressure sensors 54 and valves 56 for safety reasons, a battery or other power supply for powering the monitor 50, a memory module for storing program code (for example for executing any of the methods described herein) and/or the BP measurements, a communication module for enabling the BP measurements to be communicated to a base unit for the monitor 50 or a remote computer, and/or one or more user interface components that allow a user (e.g. the subject or healthcare professional) to interact and control the monitor). Also, in embodiments of the invention particularly the physiological parameter sensor 64 need not form part of the NIBP monitor as such, with instead the NIBP monitor 50 being arranged to obtain information on the physiological parameter of the subject from a separately provided physiological parameter sensor 64.

Figure 4:
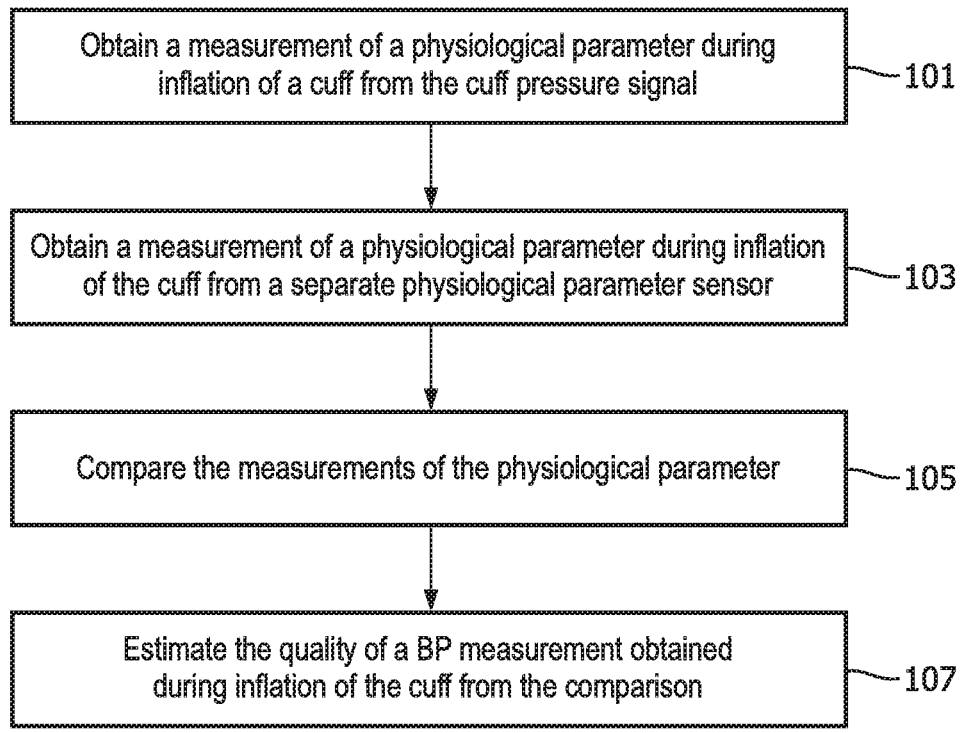
FIG. 4 is a flow chart illustrating a method of operating a NIBP monitor according to an aspect of the invention.

The flow chart in FIG. 4 illustrates a method of operating a NIBP monitor 50 according to this aspect of the invention. In a first step, step 101, which takes place when the cuff 58 is being inflated in order to take a BP measurement using an inflation-based algorithm, a measurement of a physiological parameter of the subject is obtained from the pressure signal representing the pressure in the cuff 58. This measurement of the physiological parameter is referred to as the 'first' measurement herein. The accuracy of the first measurement can be affected by, for example, movements of the subject while the cuff 58 is being inflated. As noted above, in preferred embodiments the physiological parameter is the heart rate, pulse rate or a signal representing the heart beats of the subject. In these preferred embodiments, the pressure signal can be processed to determine the heart or pulse rate of the subject by estimating the autocorrelation function of the pressure signal and then finding a peak in that function that most likely corresponds to the subject's heart rate. In some cases the amplitude of the peak can be compared to a threshold to determine if the peak has a sufficient magnitude to represent the heart rate. If the amplitude of the peak exceeds the threshold, the peak can be used as the estimate of the heart rate. Those skilled in the art will be aware of other ways in which the pressure signal can be processed to obtain a measurement of the heart or pulse rate of the subject.

In the second step 103, which as described below takes place at generally the same time as step 101 (and thus takes place during inflation of the cuff 58), a measurement of the physiological parameter of the subject is obtained using the sensor 64. The physiological parameter measured in this step is the same physiological parameter extracted or determined from the pressure signal in step 101. The measurement of the physiological parameter obtained from the sensor 64 is referred to as the 'second' measurement herein.

As noted above steps 101 and 103 are preferably performed at generally the same time (e.g. at the same time instant or within a certain time window) so that the first measurement and second measurement are directly comparable. It will also be appreciated that it may be necessary to correct the timing of one of the first or second measurements to account for time delays in the processing of the relevant signal and extraction of the physiological parameter. For example, the timing of a signal representing the beating of the heart obtained from the pressure signal may need to be corrected to account for the delay in extracting this signal from the pressure signal compared to obtaining a heart beat signal from a dedicated heart beat sensor 64. Those skilled in the art will be aware of various ways in which the relative timings of two signals can be corrected, and therefore further details are not provided herein.

In step 105, the first measurement and the second measurement are compared with each other. Since the second measurement is obtained using a dedicated sensor, the second measurement is assumed to be reliable, and is therefore used as a 'benchmark' for the first measurement. Depending on the specific physiological parameter measured in steps 101 and 103, step 105 can comprise evaluating the numerical difference between the measurements (e.g. if the physiological parameter is a heart rate or pulse rate) or evaluating how close the first measurement matches the second measurement (e.g. if the physiological parameter is a signal representing the beating of the subject's heart) using a statistical analysis. Those skilled in the art will be aware of various ways of comparing the two measurements.

Then, in step 107, the result of the comparison in step 105 is used to estimate the quality or reliability of a BP measurement obtained during the inflation of the cuff 58. In some embodiments, step 107 can comprise comparing the difference between the first and second measurements or the result of the statistical analysis to a threshold or a range of acceptable values. If the difference between the first and second measurements is below the threshold (i.e. the measurements are the same or similar to each other), or the result of the statistical analysis indicates that the measurements are sufficiently close to each other, then step 107 determines that a BP measurement obtained during the inflation of the cuff 58 will be reliable, and an inflation-based BP measurement can be completed. However, if the difference between the first and second measurements is above the threshold or the result of the statistical analysis indicates that the measurements are not sufficiently close to each other, then step 107 determines that a BP measurement obtained during the inflation of the cuff 58 will not be reliable. This is because the pressure signal resulted in a measurement for the physiological parameter that was too different from the 'benchmark' second measurement.

It will be appreciated that step 107 is performed without reference to an actual BP measurement, and therefore step 107 can be performed before the BP measurement has been obtained from the pressure signal (i.e. steps 105 and 107 are performed during inflation of the cuff 58 and before the pressure required to complete the BP measurement is reached), since the artefacts present in the pressure signal which lead to the first measurement being sufficiently different to the second measurement will prevent an accurate measurement of BP being obtained. Alternatively, step 107 can be performed once the BP measurement has been obtained, for example before the control unit 62 opens the valve 56 to deflate the cuff 58 or after the BP measurement process has been completed and the cuff 58 deflated.

In some embodiments, if step 107 indicates that a BP measurement obtained during inflation of the cuff 58 will be (or is) unreliable, the method can further comprise discarding the BP measurement or marking it as unreliable (for example the result can be flagged as unreliable on an output display or in a database that stores the BP measurements). Alternatively, if step 107 indicates that a BP measurement obtained during inflation of the cuff 58 will be (or is) unreliable, the method can further comprise obtaining a BP measurement using a conventional deflation-based BP algorithm. In this case, it is preferable for step 107 to be completed before the cuff 58 is deflated at the end of the inflation-based measurement, so that the deflation-based measurement can be performed straight away to minimize the time impact on the subject.

BP Measurement Schedule Adaptation

Another aspect of the invention provides a method for adapting a schedule for BP measurements to avoid taking BP measurements when the reliability of the BP measurement is likely to be low. This aspect is particularly useful for subjects that have frequent or near continuous BP measurements taken by a monitor. This aspect can be combined with the aspect described above and shown in FIG. 4 in order to adjust the timing of scheduled measurements or the manner in which the scheduled measurement is performed, or it can be implemented separately to the above aspect. In particular, in certain embodiments, this aspect can be implemented using the NIBP monitor shown in FIG. 3.

Figure 5:
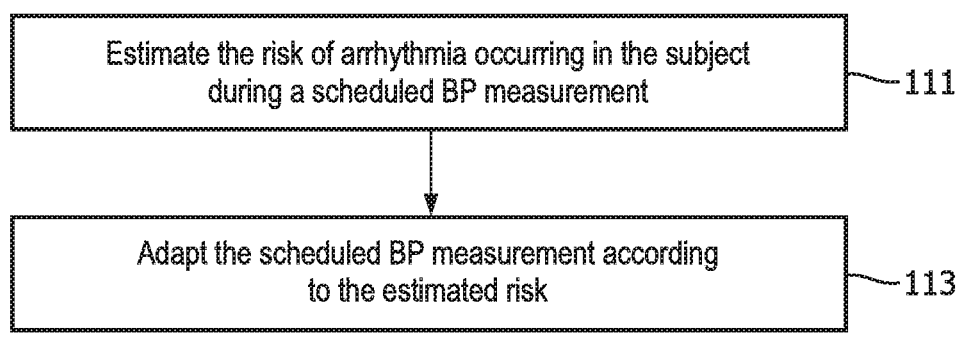
FIG. 5 is a flow chart illustrating a method of operating a NIBP monitor according to another aspect of the invention.

It has been recognized that an arrhythmia occurring during an inflation-based BP measurement will affect the accuracy of the BP measurement (or make obtaining a reasonable BP measurement impossible). Therefore, this aspect of the invention provides (as shown in FIG. 5) that the risk of an arrhythmia occurring in a subject during a BP measurement scheduled for a particular time is estimated (step 111) and the scheduled BP measurement is adapted (step 113) according to the estimated risk.

In some embodiments, step 113 comprises rescheduling the scheduled BP measurement (which includes delaying or postponing the scheduled BP measurement) to a different time if the risk of an arrhythmia occurring during the BP measurement is too high (e.g. if the risk is above a threshold). In other embodiments, step 113 comprises performing a deflation-based BP measurement at the scheduled time rather than an inflation-based measurement if the risk is too high (since a deflation-based measurement is less susceptible to arrhythmias), and likewise performing an inflation-based measurement at the scheduled time rather than a deflation-based measurement if the risk is sufficiently low (i.e. below the threshold).

It will be appreciated that in some embodiments, step 111 can be performed just before a scheduled BP measurement is due to take place.

The frequency with which BP measurements are to be taken can be different for each subject (for example once per hour, once per day, etc.), and the NIBP monitor can be programmed with an appropriate measurement schedule for the subject.

In some embodiments, step 111 uses a statistical learning procedure that infers the status of the subject over a longer monitoring interval to estimate the risk of an arrhythmia occurring during a scheduled BP measurement. For example, the statistical learning procedure could make use of pattern recognition techniques that analyze previous occurrences of arrhythmias in the subject to estimate when future arrhythmias are likely to occur. Arrhythmias in the subject can be detected by analyzing measurements from a physiological parameter sensor (such as a heart rate sensor), such as sensor 64 in the monitor 50 shown in FIG. 3 or a sensor in a device other than the NIBP monitor.

In some cases the risk of arrhythmia may be linked to the subject's situation (e.g. recent activity, posture, etc.), in which case step 111 can make use of information on the subject's recent activity and/or posture. This information can be obtained using the sensor 64 in the monitor 50 (particularly in the case of the sensor 64 being an accelerometer), or from another sensor (e.g. an accelerometer) that is attached to the body of the subject.

Figure 6:
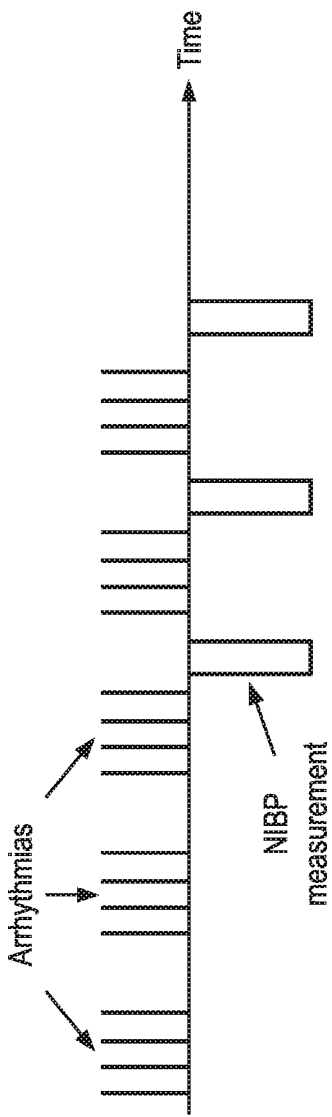
FIG. 6 illustrates an embodiment of the invention where a pattern of arrhythmias is detected and the BP measurements scheduled accordingly.

FIG. 6 illustrates an embodiment of the invention where a pattern of arrhythmias is detected and the BP measurements scheduled accordingly. Thus it can be seen that in this case the arrhythmias occur generally periodically, which can be recognized by the pattern recognition algorithm, and BP measurements are scheduled at times where the pattern recognition algorithm estimates that the risk of arrhythmias occurring is sufficiently low. Alternatively, as noted above, if a scheduled BP measurement falls in a period where the risk of arrhythmia is high, the scheduled BP measurement can be adapted so that it is performed as a deflation-based BP measurement rather than an inflation-based measurement.

In some cases, the risk of arrhythmia is linked to the current posture of the subject. In this case, step 111 can comprise determining the current posture of the subject (e.g. from an accelerometer signal), and if the subject is in an inappropriate posture or a non-preferred posture for the BP measurement, step 113 can comprise, for example, delaying or postponing the BP measurement until the subject is in an appropriate posture for the BP measurement (or in a posture that does not carry such a high risk of arrhythmias). In some embodiments, feedback on the subject's posture may be provided to the subject to encourage the subject to adopt a more appropriate or the correct posture. Alternatively step 113 can comprise performing the BP measurement as a deflation-based measurement rather than an inflation-based measurement. Those skilled in the art will be aware of various ways in which the posture of the subject can be determined. For example, in one implementation, an accelerometer can be attached to the subject and the direction of gravity measured by the accelerometer can be used as a simple estimate of the posture (for example, upright, lying on their front, back, left side or right side).

Figure 7:
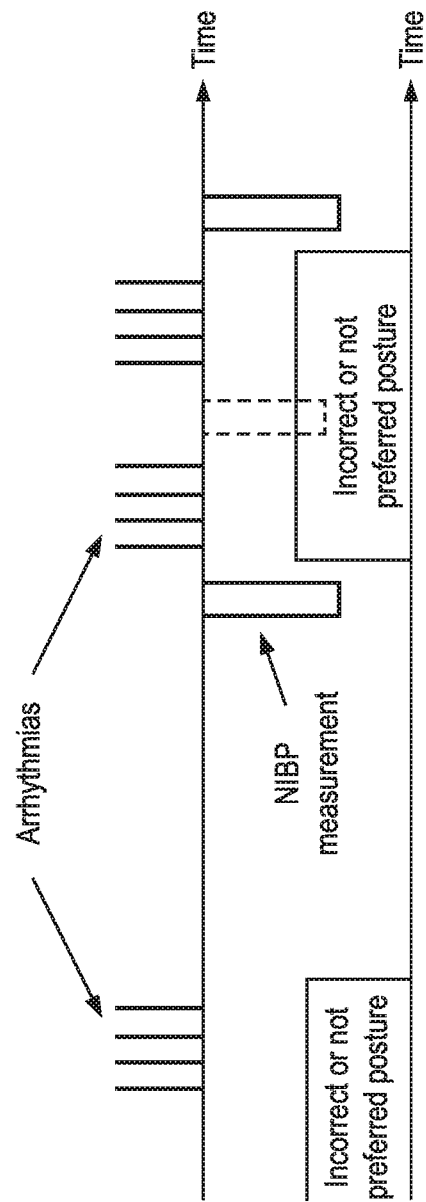
FIG. 7 illustrates an embodiment of the invention where the risk of arrhythmias is linked to the posture of the subject.

FIG. 7 illustrates an embodiment of the invention where the risk of arrhythmias is linked to the posture of the subject. Here, the posture of the subject is measured, and when an 'incorrect' posture or a non-preferred posture for the BP measurement is detected, any scheduled BP measurement (indicated by the dashed box in FIG. 7) occurring while the subject is in that posture can be rescheduled for a later time when the subject is in an appropriate posture. It will be appreciated that in this embodiment pattern recognition algorithms can be used to identify the postures that lead to a higher risk of arrhythmias in the subject, as well as identifying patterns in the postures of the subject throughout the day, and thus schedule the BP measurements accordingly. Alternatively, as noted above, if a scheduled BP measurement falls in a period where the subject is in an incorrect or inappropriate posture for the BP measurement (i.e. the risk of arrhythmia is high), the scheduled BP measurement can be adapted so that it is performed as a deflation-based BP measurement rather than an inflation-based measurement. In some embodiments, as noted above, prior to rescheduling the BP measurement or changing the type of BP measurement to be performed in response to an incorrect posture being detected, the NIBP monitor can inform the subject that they are in an incorrect posture or request the subject to change to the correct posture. In that case, if the subject changes to the correct posture, the BP measurement can be performed according to the schedule.

In some cases, the risk of arrhythmia is linked to the recent or current physical activity level of the subject. In this case, step 111 can comprise determining the recent or current activity level of the subject (for example using an accelerometer), and if the subject has recently engaged in an activity, or is currently engaged in an activity, step 113 can comprise, for example, delaying or postponing the BP measurement until a sufficient time has passed from the activity that the subject is at an acceptably low risk of arrhythmia. Alternatively step 113 can comprise performing the scheduled BP measurement as a deflation-based measurement rather than an inflation-based measurement. Those skilled in the art will be aware of various ways in which the activity level of the subject can be determined. It will be appreciated that in this embodiment pattern recognition algorithms can be used to identify activities or activity levels that lead to a higher risk of arrhythmias in the subject, as well as identifying patterns in the activities of the subject throughout the day, and thus schedule the BP measurements accordingly.

Exemplary Techniques for Measuring the BP During Inflation of the Cuff

Two exemplary techniques for measuring the BP during inflation of the cuff 58 are described below with reference to FIGS. 8 and 9. Either of these techniques, or other techniques known to those skilled in the art can be used in either or both of the aspects described above.

Figure 8:
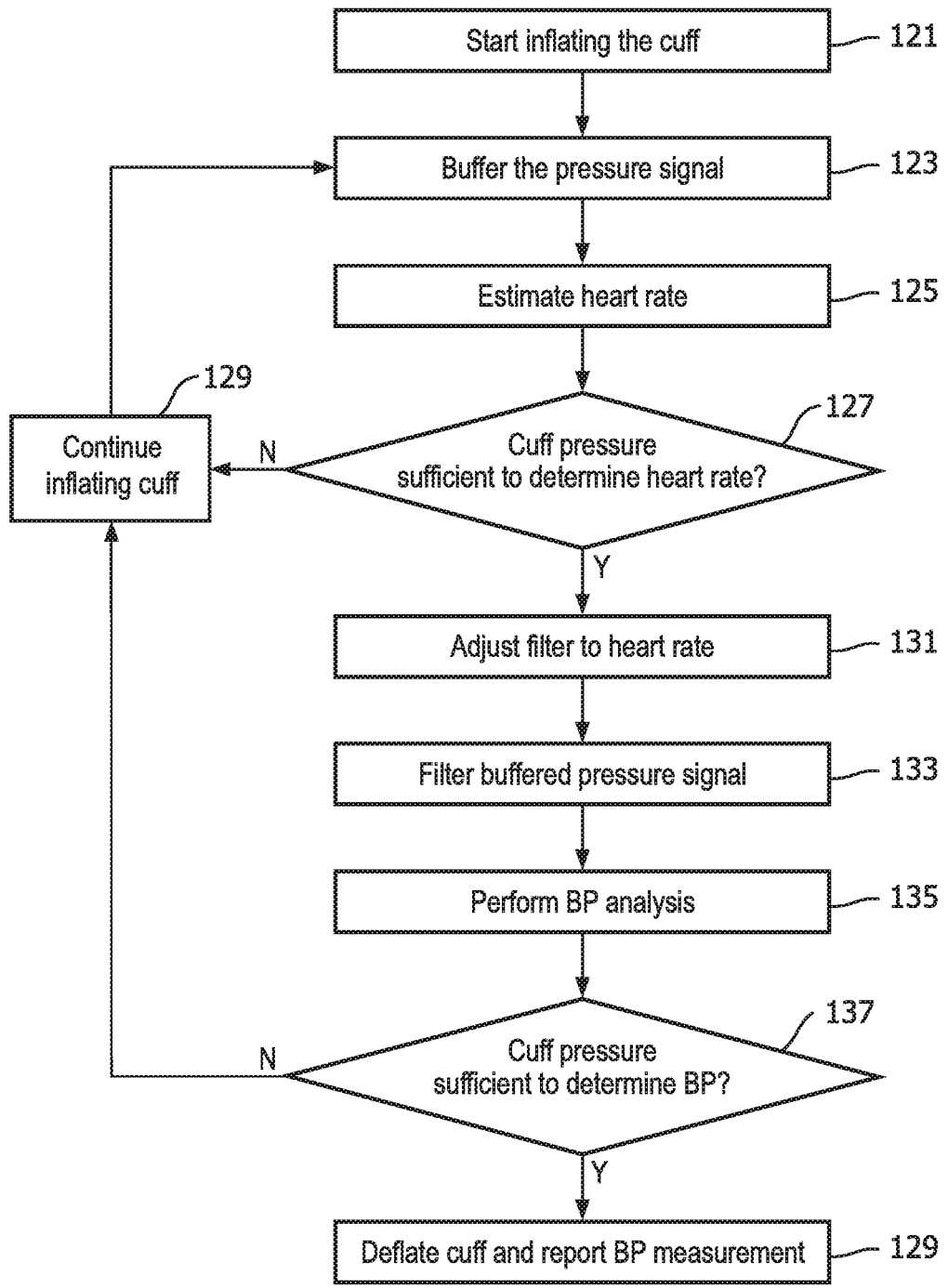
FIG. 8 is a flow chart illustrating an exemplary method for performing an inflation-based BP measurement.

FIG. 8 illustrates an exemplary method for measuring the BP during inflation of the cuff 58. Briefly, in this method, information about the subject's heart rate is obtained from the pressure signal and used to adapt a filter that is applied to the pressure signal in order to obtain the BP measurement. This method can be implemented using the monitor 50 shown in FIG. 3.

In step 121 inflation of the cuff 58 is started, and the pressure signal representing the pressure in the system is buffered (step 123). In order to obtain a reliable BP measurement, the subject's blood pressure range (diastolic to systolic) needs to be sampled over a certain number of heart cycles (beats). This certain number of heart cycles puts an upper limit on the rate at which the cuff can be inflated from the diastolic pressure to the systolic pressure (since if the cuff is inflated too quickly there will not be enough heart cycles in the signal representing the pressures between diastolic and systolic pressure to obtain a reliable BP measurement). Thus, in step 121 the cuff 28 is inflated at a rate that will allow a sufficient number of heart cycles in the diastolic to systolic range to be measured (typically this rate is set based on an assumption of the lowest possible heart rate in order to ensure that a sufficient number of heart cycles are captured).

In step 125, the buffered pressure signal is processed to determine the heart rate of the subject. This step typically requires a substantial length or duration of pressure signal (e.g. covering a few heart beats) in order to be able to extract the heart rate information. If the pressure in the cuff is not yet sufficient to determine the heart rate (as determined in step 127), then no heart rate will be determined in step 125, and the method passes to step 129 in which inflation of the cuff 58 continues and the pressure signal continues to be buffered (step 123). It will be appreciated that where the physiological parameter measured in step 101 is the heart rate, step 101 will be performed during the inflation-based BP measurement algorithm (i.e. in step 125), so no separate step 101 may be required in order to implement this aspect of the invention. In some embodiments, step 125 can comprise estimating the autocorrelation function of the buffered pressure signal and then finding a peak in that function that most likely corresponds to the subject's heart rate. In some cases the amplitude of the peak can be compared to a threshold to determine if the peak has a sufficient magnitude to represent the heart rate. If the amplitude of the peak exceeds the threshold, the peak can be used as the estimate of the heart rate.

If the heart rate can be extracted from the pressure signal in step 125, the method passes to step 131 in which the heart rate is used to adapt a filter that is to be applied to the pressure signal. Once the filter has been adapted to the heart rate of the subject, the buffered pressure signal can be filtered (step 133) and an analysis of the filtered pressure signal performed to determine the BP (step 135). The filter is a high-pass filter, similar to the high-pass filter used in the traditional oscillometric method. The heart rate (HR) is used to adapt the frequency characteristics of the filter, e.g. the cut-off frequency. In some embodiments, the cut-off frequency can be set to the heart rate (e.g. 60 beats per minute, bpm=1 Hz), but in other embodiments the cut-off frequency may be (slightly) higher or lower than the heart rate (depending on details of the filter design and other processing steps). Generally, the higher the heart rate, the higher the cut-off frequency of the filter (and vice versa). In one example, a basic moving average filter is used, whereby the width of the averaging window is set to correspond to the heart period (=1/HR). Running this filter over the pressure signal returns a low-pass filtered pressure signal, which is then subtracted from the original pressure signal to obtain the high-pass filtered pressure signal.

If the pressure in the cuff 58 is not yet sufficient to determine the BP (e.g. if the cuff pressure has not yet reached the systolic pressure) then the inflation of the cuff continues (step 129). At this stage, as the heart rate has already been determined, it may not be necessary to continue processing the pressure signal to extract the current heart rate (step 125) and adapt the filter (step 131), so the method can return to step 133 after step 129 and the filter can be applied to newly buffered pressure signal data. In other implementations, the extraction of the heart rate and adaptation of the filter can be a continuous process, in which case the method can return to step 123. If at step 135 a BP measurement is determined from the pressure signal, then the method passes to step 139 in which the inflation of the cuff 58 by the pump 52 is stopped, the cuff 58 is deflated and the BP measurement can be reported to the subject, other operator of the monitor 50 or a remote computer or base unit that collates and stores the BP measurement information for the subject.

Figure 9:
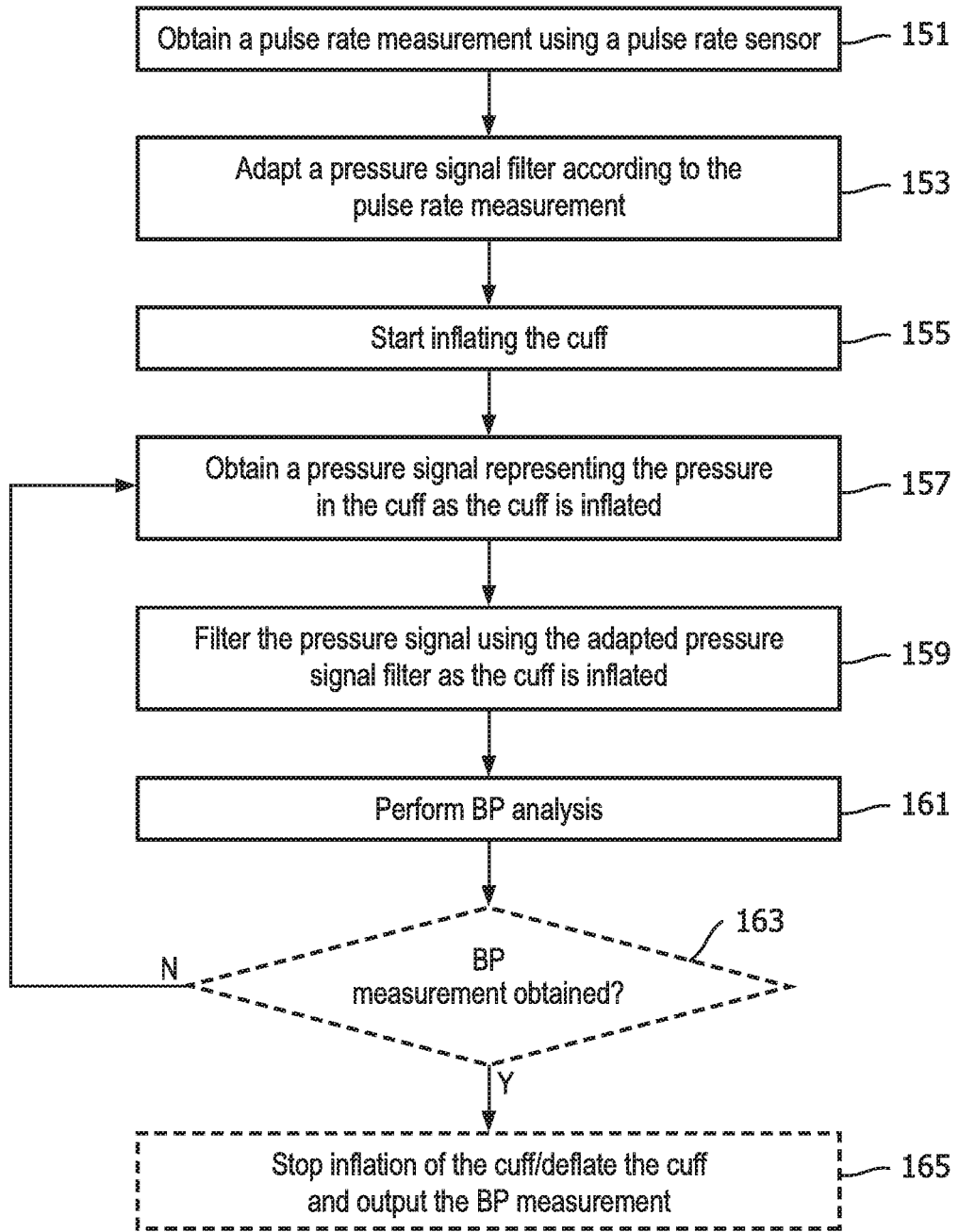
FIG. 9 is a flow chart illustrating an alternative method for performing an inflationary-based BP measurement.

An alternative technique for measuring BP during inflation of a cuff is shown in FIG. 9. This method can be implemented by a NIBP monitor 50 as shown in FIG. 3.

In the first step, step 151, the pulse rate sensor 64 is used to obtain a measurement of the pulse rate of the subject. This step is first performed at the start of the BP measurement process, preferably just prior to starting the inflation of the cuff 58 by pump 52, although in some embodiments it can be performed as, or just after, inflation of the cuff 58 is started. In any case, the measurement of the pulse rate is available much earlier in the process than in the previous exemplary method in which the pulse rate information has to be derived from the pressure signal.

Once the measurement of the pulse rate has been obtained, the filter that is applied to the pressure signal as part of the process for determining the BP measurement is adapted according to the pulse rate measurement (step 153). As in the method of FIG. 8, in step 153 the filter can be a high-pass filter, similar to the high-pass filter used in the traditional oscillometric method. The pulse rate (PR) is used to adapt the frequency characteristics of the filter, e.g. the cut-off frequency. In some embodiments, the cut-off frequency can be set to the heart rate (e.g. 60 beats per minute, bpm=1 Hz), but in other embodiments the cut-off frequency may be set (slightly) higher or lower than the heart rate (depending on details of the filter design and other processing steps). Generally, the higher the heart rate, the higher the cut-off frequency of the filter (and vice versa). In one example, a basic moving average filter is used, whereby the width of the averaging window is set to correspond to the heart period (=1/PR). Running this filter over the pressure signal returns a low-pass filtered pressure signal, which is then subtracted from the original pressure signal to obtain the high-pass filtered pressure signal.

The inflation of the cuff 58 is started (step 155) and a pressure signal representing the pressure in the cuff 58 is obtained (step 157).

Next, this pressure signal is filtered using the adapted filter (step 159). This filtering is performed during inflation of the cuff 58, and preferably in real time as the pressure signal is obtained (or as near to real time as is possible). The filtered pressure signal is then analyzed to determine the BP measurement (step 161). Those skilled in the art will be aware of various techniques for performing this analysis, and therefore further details are not provided herein. Again, this step is performed during inflation of the cuff 58, and preferably in real time (or as near to real time as is possible).

If a BP measurement cannot be obtained from the pressure signal (e.g. if the pressure in the cuff 58 has not yet reached the systolic blood pressure in the subject), then following step 143 the inflation of the cuff 58 continues and the method returns to step 137 where the pressure signal continues to be obtained, filtered and analyzed. If a BP measurement is obtained in step 161, the method passes to step 165 in which the inflation of the cuff 58 is stopped and the deflation of the cuff 58 is started (e.g. by opening valve 56). Since the BP measurement has been obtained, the deflation is preferably performed as fast as possible. The deflation is preferably initiated as soon as or immediately after the BP measurement has been obtained. The BP measurement can be reported to the subject, other operator of the monitor 50 or a remote computer or base unit that collates and stores the BP measurement information for the subject.

There is therefore provided an NIBP monitor and method of operating the same that can measure the blood pressure during inflation of the cuff and that provides improved accuracy of the blood pressure measurement compared to conventional monitors.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of operating a non-invasive blood pressure, NIBP, monitor to measure the blood pressure of a subject, comprising:
   determining a pattern of arrhythmias for the subject based on historical pulse or heart rate measurements;
   during each of a plurality of blood pressure measurements of the subject:
      predicting, based on the pattern of arrhythmias for the subject, a likelihood that the subject will experience an arrhythmia during inflation of a cuff that is placed around a limb of the subject;
      in response to a determination that the likelihood that the subject will experience an arrhythmia during inflation of the cuff does not satisfy a threshold:
         buffering a pressure signal output by a pressure sensor associated with the cuff, wherein the buffering is performed during inflation of the cuff;
         processing the buffered pressure signal across a plurality of heart beats of the subject to estimate an autocorrelation function of the buffered pressure signal;
         identifying a plurality of peaks in the autocorrelation function;
         determining a heart rate of the subject based on the plurality of peaks;
         adapting one or more frequency characteristics of a high-pass filter based on the heart rate;
         applying the filter to the buffered pressure signal to generate a filtered pressure signal;
         analyzing the filtered pressure signal to determine an inflation-based blood pressure measurement for the subject; and
         deflating the cuff over a first time interval without obtaining a deflation-based blood pressure measurement during the deflating; or
      in response to a determination that the likelihood that the subject will experience an arrhythmia during inflation of the cuff satisfies the threshold:
         causing inflation of the cuff;
         deflating the cuff over a second time interval that is longer than the first time interval,
         obtaining a deflation-based blood pressure measurement during the deflating, and
         providing the deflation-based blood pressure measurement as output.

2. The method of claim 1, wherein the pattern of arrhythmias are further determined based on one or more past postures of the subject during acquisition of the historical pulse or heart rate measurements, and wherein the predicting is further based on a current posture of the subject.

3. The method of claim 1, wherein the pattern of arrhythmias are further determined based on past activity levels of the subject during acquisition of the historical pulse or heart rate measurements, and wherein the predicting is further based on a current or recent activity level of the subject.

4. A non-invasive blood pressure, NIBP, monitor for measuring the blood pressure of a subject, the NIBP monitor comprising:
   a control unit that is configured to:
      determine a pattern of arrhythmias for the subject based on historical pulse or heart rate measurements of the subject; and
      during each of a plurality of scheduled blood pressure measurements of the subject:
         predict, based on the pattern of arrhythmias for the subject, a likelihood that the subject will experience an arrhythmia during inflation of a cuff that is placed around a limb of the subject;
         in response to a determination that the likelihood that the subject will experience an arrhythmia during inflation of the cuff does not satisfy a threshold:
            buffer a pressure signal output by a pressure sensor associated with the cuff, wherein the buffering is performed during inflation of the cuff;
            process the buffered pressure signal across a plurality of heart beats of the subject to estimate an autocorrelation function of the buffered pressure signal;
            identify a plurality of peaks in the autocorrelation function;
            determine a heart rate of the subject based on the plurality of peaks;
            adapt one or more frequency characteristics of a high-pass filter based on the heart rate;
            apply the filter to the buffered pressure signal to generate a filtered pressure signal;
            analyze the filtered pressure signal to determine an inflation-based blood pressure measurement for the subject; and
            deflate the cuff over a first time interval without obtaining a deflation-based blood pressure measurement during the deflating; or
         in response to a determination that the likelihood that the subject will experience an arrhythmia during inflation of the cuff satisfies the threshold:
            cause inflation of the cuff;
            deflate the cuff over a second time interval that is longer than the first time interval, obtain a deflation-based blood pressure measurement during the deflating, and provide the deflation-based blood pressure measurement as output.

5. At least one non-transitory computer-readable medium comprising instructions that, in response to execution of the instructions by one or more processors of a non-invasive blood pressure, NIBP, monitor for measuring the blood pressure of a subject, cause the one or more processors to perform the following operations:

determining a pattern of arrhythmias for the subject based on historical pulse or heart rate measurements;

during each of a plurality of blood pressure measurements of the subject:

predicting, based on the pattern of arrhythmias for the subject, a likelihood that the subject will experience an arrhythmia during inflation of a cuff that is placed around a limb of the subject;

in response to a determination that the likelihood that the subject will experience an arrhythmia during inflation of the cuff does not satisfy a threshold:

buffering a pressure signal output by a pressure sensor associated with the cuff, wherein the buffering is performed during inflation of the cuff;

processing the buffered pressure signal across a plurality of heart beats of the subject to estimate an autocorrelation function of the buffered pressure signal;

identifying a plurality of peaks in the autocorrelation function;

determining a heart rate of the subject based on the plurality of peaks;

adapting one or more frequency characteristics of a high-pass filter based on the heart rate;

applying the filter to the buffered pressure signal to generate a filtered pressure signal;

analyzing the filtered pressure signal to determine an inflation-based blood pressure measurement for the subject; and deflating the cuff over a first time interval without obtaining a deflation-based blood pressure measurement during the deflating; or in response to a determination that the likelihood that the subject will experience an arrhythmia during inflation of the cuff satisfies the threshold:

causing inflation of the cuff;

deflating the cuff over a second time interval that is longer than the first time interval, obtaining a deflation-based blood pressure measurement during the deflating, and providing the deflation-based blood pressure measurement as output.

* * * * *